(12) United States Patent
Baig et al.

(10) Patent No.: US 11,752,224 B2
(45) Date of Patent: Sep. 12, 2023

(54) REFRIGERATOR APPLIANCE AND SANITIZER ASSEMBLY

(71) Applicant: Haier US Appliance Solutions, Inc., Wilmington, DE (US)

(72) Inventors: Mirza Yaseen Baig, Hyderabad (IN); Roobanprasath P., Hyderabad (IN)

(73) Assignee: Haier US Appliance Solutions, Inc., Wilmington, DE (US)

(*) Notice: Subject to any disclaimer, the term of this patent is extended or adjusted under 35 U.S.C. 154(b) by 218 days.

(21) Appl. No.: 17/172,542

(22) Filed: Feb. 10, 2021

(65) Prior Publication Data
US 2022/0249713 A1   Aug. 11, 2022

(51) Int. Cl.
| A61L 2/07 | (2006.01) |
| F25D 23/02 | (2006.01) |
| A61L 2/24 | (2006.01) |
| A61L 2/00 | (2006.01) |

(52) U.S. Cl.
CPC .............. *A61L 2/07* (2013.01); *A61L 2/0023* (2013.01); *A61L 2/24* (2013.01); *F25D 23/028* (2013.01); *A61L 2202/11* (2013.01); *A61L 2202/122* (2013.01); *A61L 2202/14* (2013.01)

(58) Field of Classification Search
CPC ..... A61L 2/07; A61L 2/24; A61L 2/26; A61L 2/0023; A61L 2202/11; A61L 2202/122; A61L 2202/14; A61L 2202/182; F25D 23/12; F25D 23/028; F25D 2400/02

See application file for complete search history.

(56) References Cited

U.S. PATENT DOCUMENTS

| 5,476,525 | A | * | 12/1995 | Bekedam | B01D 47/021 |
| | | | | | 137/171 |
| 8,499,579 | B2 | | 8/2013 | Luisi et al. | |
| 9,638,461 | B2 | * | 5/2017 | Wait | B67D 1/0014 |
| 2005/0031510 | A1 | * | 2/2005 | Hasegawa | A61L 2/26 |
| | | | | | 422/26 |
| 2006/0222579 | A1 | * | 10/2006 | Kim | A61L 2/26 |
| | | | | | 422/26 |
| 2007/0003461 | A1 | | 1/2007 | Kim | |
| 2015/0060491 | A1 | * | 3/2015 | Bird | F25D 23/126 |
| | | | | | 222/146.6 |
| 2020/0114032 | A1 | * | 4/2020 | Spencer | A61L 2/07 |
| 2020/0237939 | A1 | * | 7/2020 | Henniges | G01K 3/04 |

FOREIGN PATENT DOCUMENTS

| CN | 105003897 A | | 10/2015 |
| JP | 2004222816 A | * | 8/2004 |
| KR | 2009/0006437 U | | 6/2009 |
| KR | 2012/0011453 A | | 2/2012 |
| WO | WO2016/155406 A1 | | 10/2016 |

* cited by examiner

Primary Examiner — Jennifer Wecker
Assistant Examiner — Brady C Pilsbury
(74) Attorney, Agent, or Firm — Dority & Manning, P.A.

(57) ABSTRACT

A refrigerator appliance or sanitizer assembly may include a heating plate and a storage container. The heating plate may be mounted on a door of the refrigerator appliance. The storage container may be disposed on the heating plate and extend between a bottom end and a top end. The storage container may define a sanitization chamber above the heating plate and a container opening at the top end to permit access to the sanitization chamber.

16 Claims, 6 Drawing Sheets

REFRIGERATOR APPLIANCE AND SANITIZER ASSEMBLY

FIELD OF THE INVENTION

The present subject matter relates generally to refrigerator appliances, and more particularly to sanitization assemblies thereof for sanitizing, sterilizing, or otherwise cleaning household utensils.

BACKGROUND OF THE INVENTION

Refrigerator appliances generally include a cabinet that defines one or more chilled chambers for receipt of food articles for storage. In addition, refrigerator appliances also generally include a door rotatably hinged to the cabinet to permit selective access to food items stored in chilled chamber(s). Typical refrigerator appliances include an icemaker or other features for generating or maintaining items at a low temperature state. Additionally or alternatively, a water dispenser may be provided for dispensing relatively cool water from the refrigerator appliance.

Increasingly, consumers are conscious of the bacteria, viruses, and microorganisms that can reside on household surfaces. This awareness may be especially heightened for utensils (e.g., bottles, forks, spoons, cups, etc.) that will be used to handle food or beverages that a user will consume. Although typical refrigerator appliances include various features for dispensing ice or water, existing refrigerator appliances fail to provide features that can help address concerns over sanitization or the cleanliness of a user's utensils.

As a result, it would be useful to provide a refrigerator appliance or assembly having one or more features for removing or eliminating bacteria, viruses, or microorganisms. In particular, it would be advantageous to provide an appliance or assembly having one or more features for sanitizing, sterilizing, or otherwise cleaning utensils, such as those that might be used to with or in close proximity to the refrigerator appliance.

BRIEF DESCRIPTION OF THE INVENTION

Aspects and advantages of the invention will be set forth in part in the following description, or may be obvious from the description, or may be learned through practice of the invention.

In one exemplary aspect of the present disclosure, a sanitizer assembly for a refrigerator appliance is provided. The sanitizer assembly may include a heating plate and a storage container. The heating plate may be mounted on a door of the refrigerator appliance. The storage container may be disposed on the heating plate and extend between a bottom end and a top end. The storage container may define a sanitization chamber above the heating plate and a container opening at the top end to permit access to the sanitization chamber.

In another exemplary aspect of the present disclosure, a refrigerator appliance is provided. The refrigerator appliance may include a cabinet, a door, a heating plate, and a storage container. The door may be rotatably mounted on the cabinet to selectively restrict access to a chilled chamber. The door may define a container recess. The heating plate may be mounted on the door at the container recess. The storage container may be disposed within the container recess and extend between a bottom end and a top end. The storage container may define a sanitization chamber and a container opening between the top end and the bottom end.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

DETAILED DESCRIPTION

Figure 1:
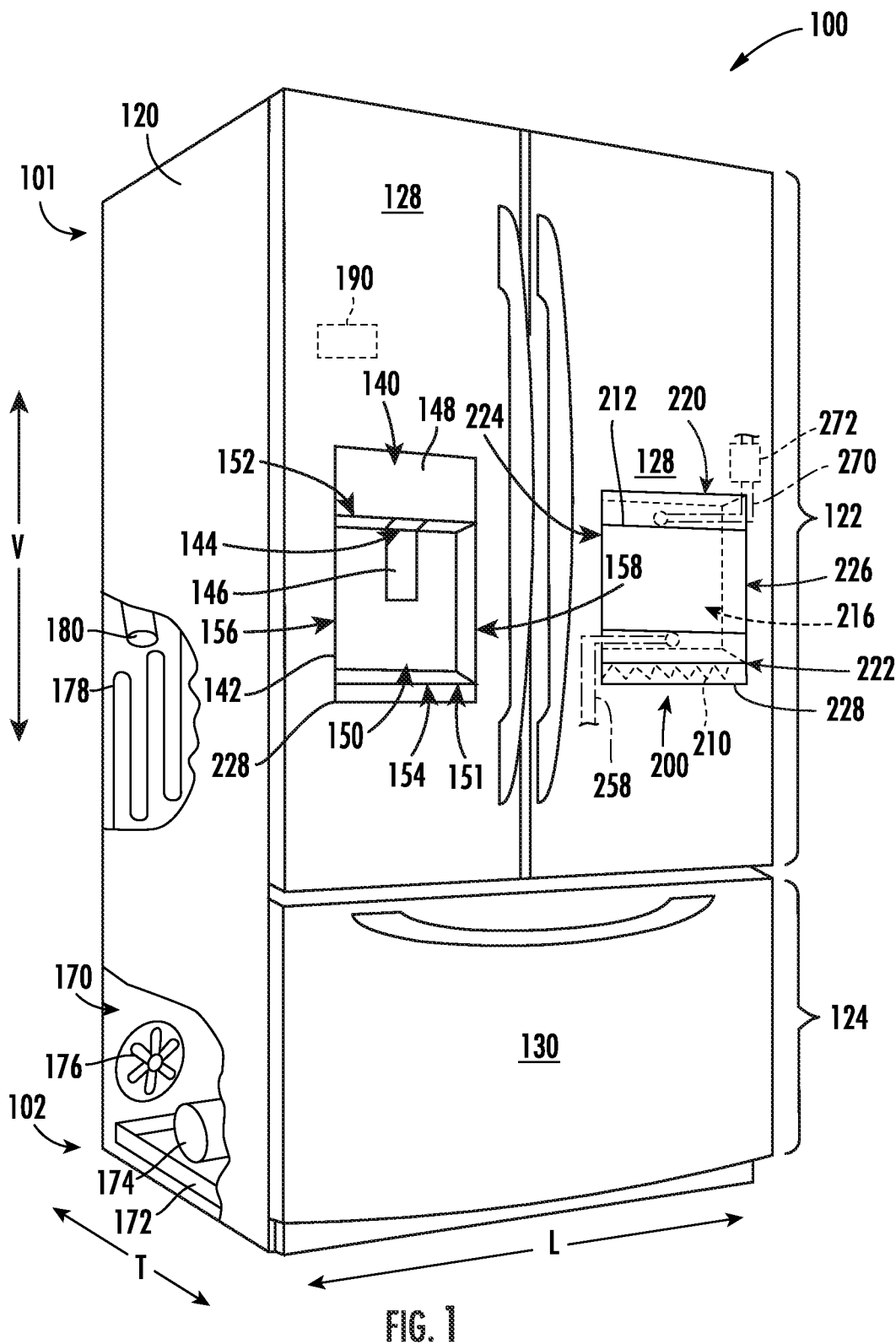
FIG. 1 provides a perspective view of a refrigerator appliance according to exemplary embodiments of the present disclosure.
Figure 2:
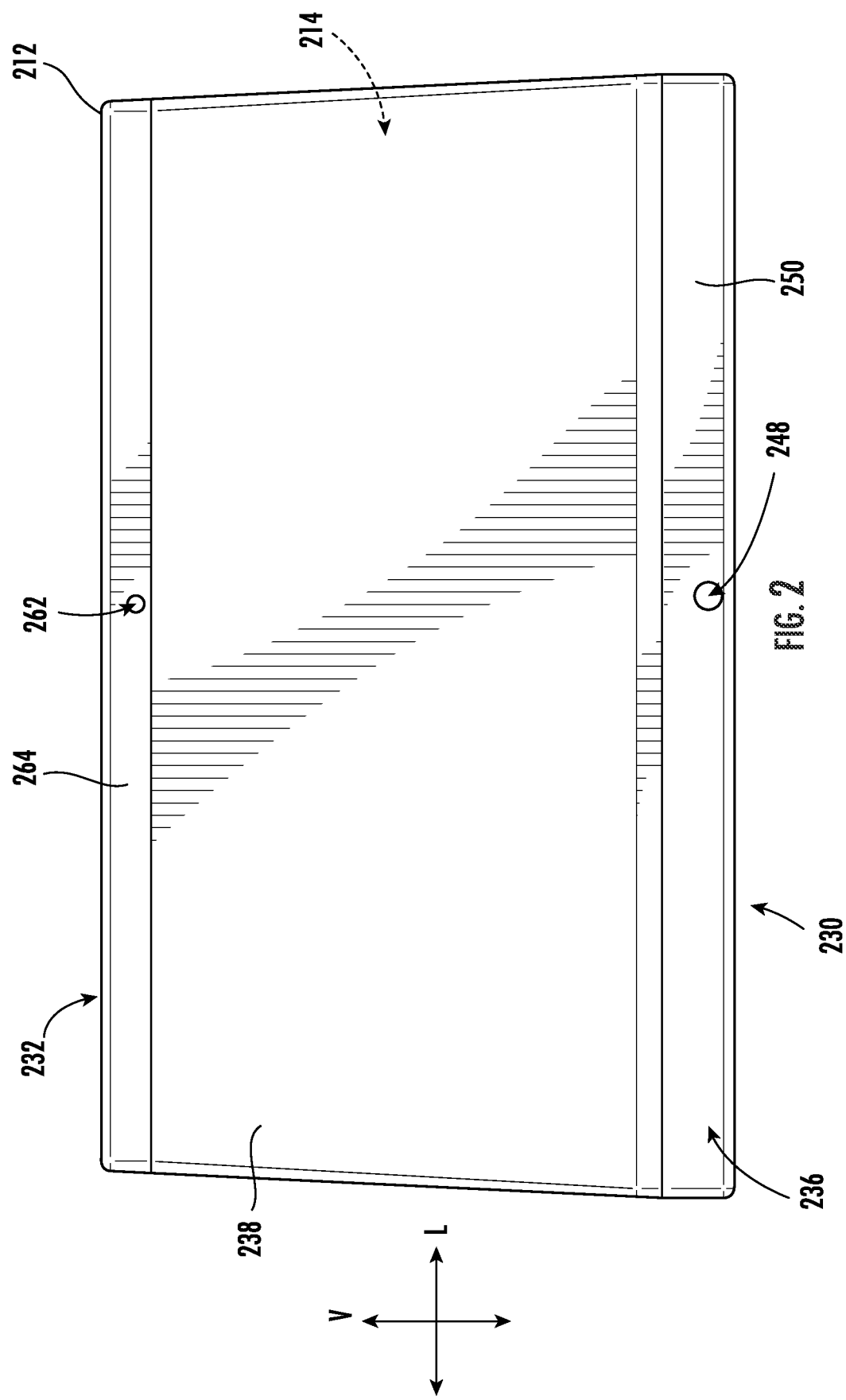
FIG. 2 provides a rear elevation view of a storage container for a refrigerator appliance according to exemplary embodiments of the present disclosure.
Figure 3:
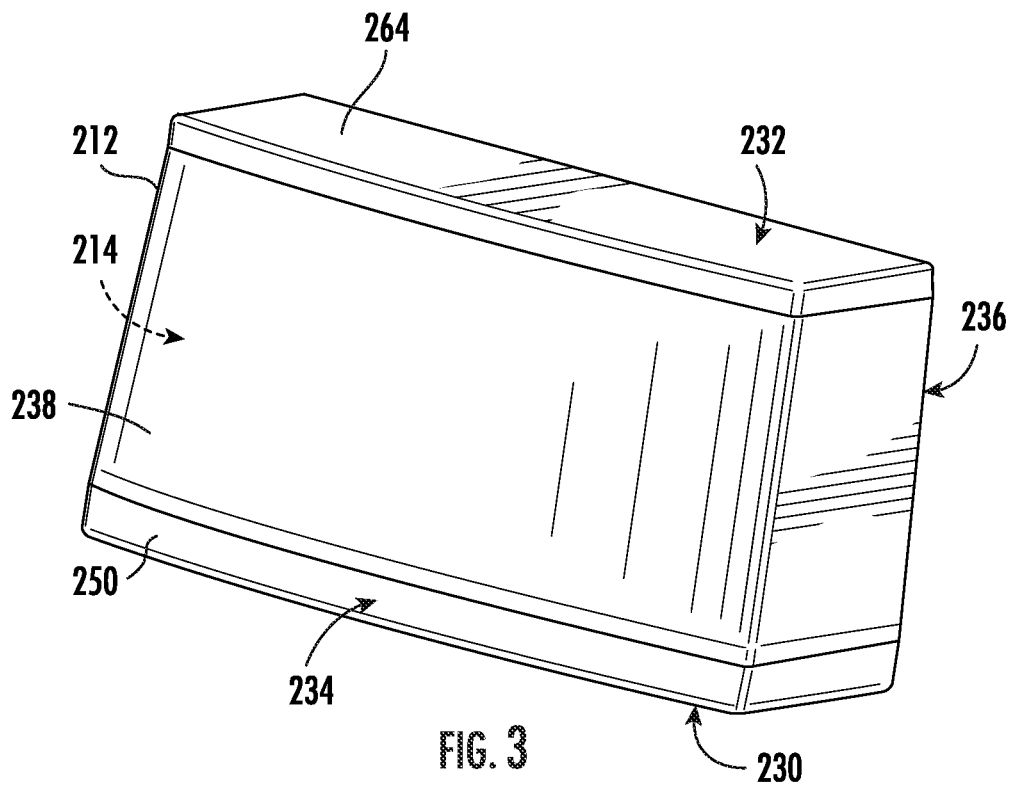
FIG. 3 provides a perspective of the exemplary storage container of FIG. 2.
Figure 4:
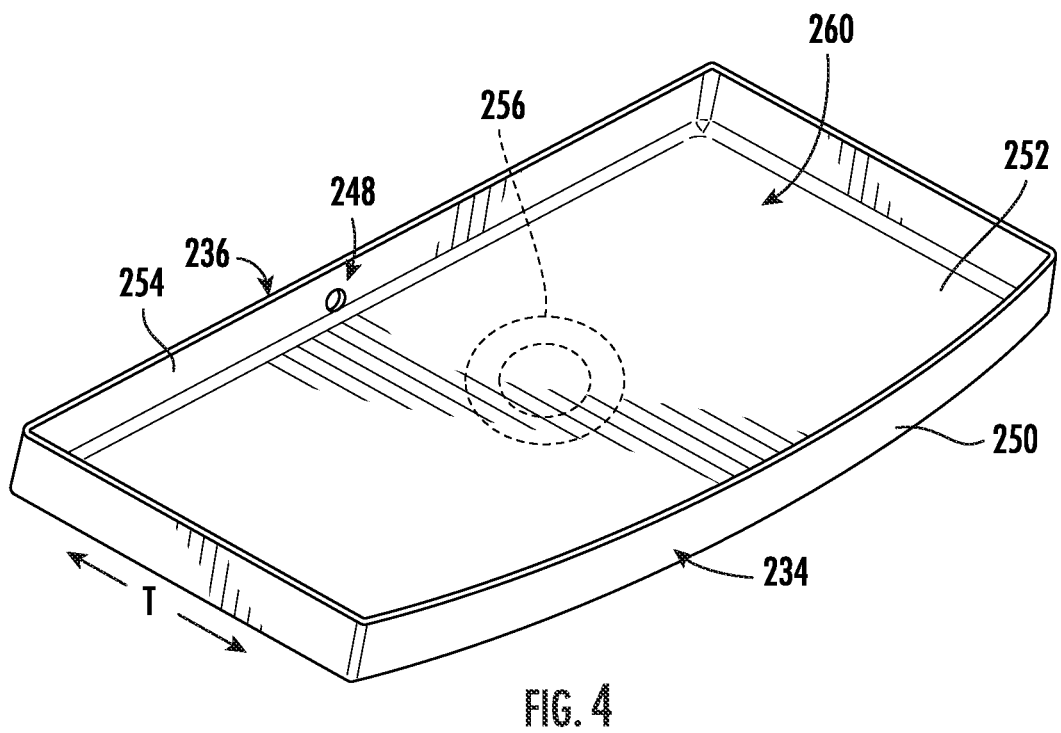
FIG. 4 provides a perspective view of a base tray, in isolation, of the exemplary storage container of FIG. 2.
Figure 5:
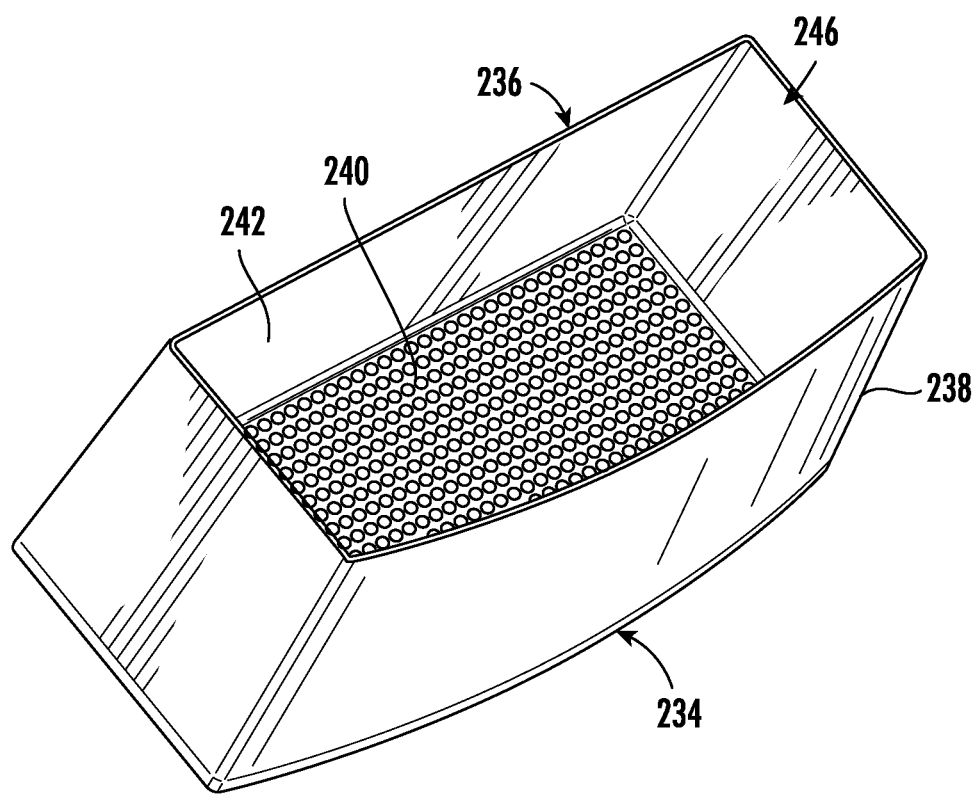
FIG. 5 provides a perspective view of a container body, in isolation, of the exemplary storage container of FIG. 2.
Figure 6:
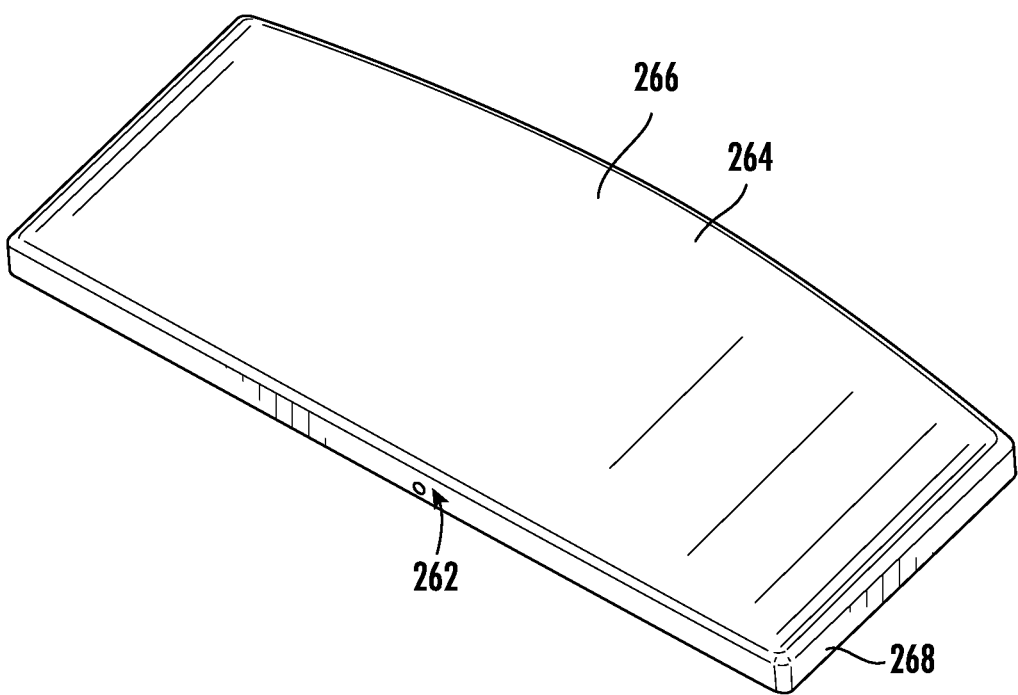
FIG. 6 provides a perspective view of a container lid, in isolation, of the exemplary storage container of FIG. 2.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the term "or" is generally intended to be inclusive (i.e., "A or B" is intended to mean "A or B or both"). The terms "first," "second," and "third" may be used interchangeably to distinguish one component from another and are not intended to signify location or importance of the individual components. The terms "upstream" and "downstream" refer to the relative flow direction with respect to fluid flow in a fluid pathway. For example, "upstream" refers to the flow direction from which the fluid flows, and "downstream" refers to the flow direction to which the fluid flows.

Referring now to the drawings, FIG. 1 provides a perspective views of a refrigerator appliance 100 according to exemplary embodiments of the present disclosure. Generally, FIG. 1 provides a pair of refrigerator doors 128 in a closed position, though such doors 128 may also be rotated to an open position (not pictured), as is understood.

Refrigerator appliance 100 includes a cabinet or housing 120 that extends between a top 101 and a bottom 102 along a vertical direction V. Cabinet 120 also extends along a lateral direction L and a transverse direction T, each of the vertical direction V, lateral direction L, and transverse direction T being mutually perpendicular to one another. Cabinet 120 defines one or more chilled chambers for receipt of food items for storage. In some embodiments, cabinet 120 defines a fresh food chamber 122 positioned at or adjacent top 101 of cabinet 120 and a freezer chamber 124 arranged at or adjacent bottom 102 of cabinet 120. As such, refrigerator appliance 100 is generally referred to as a bottom mount refrigerator. It is recognized, however, that the benefits of the present disclosure apply to other types and styles of refrigerator appliances such as, for example, a top mount refrigerator appliance or a side-by-side style refrigerator appliance. Consequently, the description set forth herein is for illustrative purposes only and is not intended to be limiting in any aspect to any particular refrigerator chamber configuration.

Refrigerator doors 128 are rotatably hinged to an edge of cabinet 120 for selectively accessing (and thus selectively restricting access to) fresh food chamber 122. In some embodiments, a freezer door 130 is arranged below refrigerator doors 128 for selectively accessing (and thus selectively restricting access to) freezer chamber 124. Freezer door 130 may be coupled to a freezer drawer (not shown) slidably mounted within freezer chamber 124. Refrigerator doors 128 and freezer door 130 are shown in the closed configuration in FIG. 1.

In some embodiments, refrigerator appliance 100 includes a dispensing assembly 140 for dispensing liquid water or ice. Dispensing assembly 140 includes a dispenser 142 (i.e., fluid dispenser) positioned on or mounted to an exterior portion of refrigerator appliance 100 (e.g., on one of doors 128). Dispenser 142 includes a discharging outlet 144 for accessing ice and liquid water. An actuating mechanism 146, shown as a paddle, is mounted below discharging outlet 144 for operating dispenser 142. In alternative exemplary embodiments, another suitable actuator may be used to operate dispenser 142. For example, dispenser 142 can include a sensor (such as an ultrasonic sensor) or a button rather than the paddle. A user interface panel 148 is provided for controlling the mode of operation. For example, user interface panel 148 includes a plurality of user inputs (not labeled), such as a water dispensing button and an ice-dispensing button, for selecting a desired mode of operation such as crushed or non-crushed ice.

Discharging outlet 144 and actuating mechanism 146 are an external part of dispenser 142 and are mounted in a dispenser recess 150, as is understood. Generally, dispenser recess 150 defines a transverse opening 151 that extends in the vertical direction V from a top recess end 152 to a bottom recess end 154, as well as in the lateral direction L from a first recess side 156 to a second recess side 158. In certain embodiments, dispenser recess 150 is positioned at a predetermined elevation convenient for a user to access ice or water and enabling the user to access ice without the need to bend-over and without the need to open doors 128. In optional embodiments, dispenser recess 150 is positioned at a level that approximates the chest level of a user.

As will be described in greater detail below, excess water from dispenser recess 150 or one or more other portions of refrigerator appliance 100 may be directed away from door 128, such as to a separate area within refrigerator appliance 100 or outside of the same (e.g., a municipal sewage system). For instance, water may be directed to an evaporation pan 172. Evaporation pan 172 is positioned within a mechanical compartment 170 defined by housing 120 (e.g., at bottom portion 102 of housing 120). A condenser 174 of the sealed system can be positioned, for example, directly, above and adjacent evaporation pan 172. Heat from condenser 174 can assist with evaporation of liquid water in evaporation pan 172. A fan 176 configured for cooling condenser 174 can also direct a flow air across or into evaporation pan 172. Thus, fan 176 can be positioned above and adjacent evaporation pan 172. Evaporation pan 172 may be sized and shaped for facilitating evaporation of liquid water therein. For example, evaporation pan 172 may be open topped and extend across about a width or a depth of housing 120.

Generally, operation of the refrigerator appliance 100 can be regulated by a controller 190 that is operatively coupled to user interface panel 148 or various other components, as will be described below. User interface panel 148 provides selections for user manipulation of the operation of refrigerator appliance 100, such as selections between whole or crushed ice, chilled water, or other various options. In response to user manipulation of user interface panel 148 or one or more sensor signals, controller 190 may operate various components of the refrigerator appliance 100. Controller 190 may include a memory and one or more microprocessors, CPUs or the like, such as general or special purpose microprocessors operable to execute programming instructions or micro-control code associated with operation of refrigerator appliance 100. The memory may represent random access memory such as DRAM, or read only memory such as ROM or FLASH. In one embodiment, the processor executes programming instructions stored in memory. The memory may be a separate component from the processor or may be included onboard within the processor. Alternatively, controller 190 may be constructed without using a microprocessor (e.g., using a combination of discrete analog or digital logic circuitry—such as switches, amplifiers, integrators, comparators, flip-flops, AND gates, and the like) to perform control functionality instead of relying upon software.

Controller 190 may be positioned in a variety of locations throughout refrigerator appliance 100. In the illustrated embodiment, controller 190 is located adjacent to or on user interface panel 148. In other embodiments, controller 190 may be positioned at another suitable location within refrigerator appliance 100, such as for example within a fresh food chamber, a freezer door, etc. Input/output ("I/O") signals may be routed between controller 190 and various operational components of refrigerator appliance 100. For example, user interface panel 148 may be in operable communication (e.g., electrical communication) with controller 190 via one or more signal lines or shared communication busses.

Controller 190 may be operatively coupled with the various components of dispensing assembly 140 and may control operation of the various components. For example, the various valves, switches, etc. may be actuatable based on commands from controller 190. As discussed, interface panel 148 may additionally be operatively coupled (e.g., via electrical or wireless communication) with controller 190. Thus, the various operations may occur based on user input or automatically through controller 190 instruction.

In certain embodiments, refrigerator appliance 100 includes a sanitizer assembly 200 having a heater 210 and storage container 212 configured to use steam to sanitize, sterilize, or otherwise clean utensils (e.g., bottles, forks, spoons, cups, etc.) placed within storage container 212. In particular, storage container 212 defines a sanitization chamber 214 within which utensils may be placed while heater 210 generates steam (e.g., during a sanitization operation) that can flow to sanitization chamber 214 to help kill or eliminate bacteria, viruses, or microorganisms on the utensils. Such a sanitization operation may, for example, be directed by controller 190 (e.g., in response to a user selection at user interface panel 148), which may be operatively coupled to heater 210 and one or more valves to control the flow of water to sanitizer assembly 200.

During use, storage container 212 can be selectively or removably disposed on refrigerator appliance 100. For instance, an assembly recess 216 that can selectively or removably receive storage container 212 may be defined on refrigerator appliance 100. In some such embodiments, assembly recess 216 defines a reception opening that extends in the vertical direction V from a top recess end 220 to a bottom recess end 222, as well as in the lateral direction L from a first recess side 224 to a second recess side 226. In certain embodiments, assembly recess 216 is positioned at a predetermined elevation convenient for a user to access storage container 212 or water and enabling the user to access ice without the need to bend-over and without the need to open doors 128. In optional embodiments, assembly recess 216 is positioned at a level that approximates the chest level of a user.

In some embodiments, a heating plate 228 of heater 210 is mounted on the door 128 proximal to assembly recess 216. Generally, heating plate 228 includes an electric element (e.g., a resistive heating element, induction heating element, halogen heating element, microwave heating element, etc.) for heating water upstream from sanitization chamber 214. Heating plate 228 may be mounted, for instance, below or directly beneath assembly recess 216 (e.g., in thermal communication therewith). Thus, storage container 212 may be selectively disposed on heating plate 228 such that heating plate 228 can heat at least a portion of storage container 212.

As shown, sanitizer assembly 200 may be provided on at least one of the refrigerator doors 128. For instance, assembly recess 216 and heating plate 228 may be included with at least one door 128. Optionally, sanitizer assembly 200 may be on a separate door 128 (or otherwise spaced apart) from dispenser 142. Alternatively, sanitizer assembly 200 may be provided proximal to dispenser 142. In some such embodiments, dispenser recess 150 is provided as or included with assembly recess 216. Heating plate 228, in turn, may be disposed beneath (e.g., directly beneath) dispenser 142 (e.g., including dispenser outlet 144 or actuating mechanism 146).

Turning now to FIGS. 2 through 6, various portions of storage container 212 are illustrated according to exemplary embodiments of the present disclosure. As noted above, storage container 212 may be selectively removably disposed on refrigerator appliance 100 (FIG. 1). Thus, storage container 212 may define a coordinate system of direction that is independent of refrigerator appliance 100. Nonetheless, as described herein, it is understood that the vertical direction V, transverse direction T, and lateral direction L described with respect to storage container 212 generally align with above-described directions of refrigerator appliance 100 when storage container 212 is disposed on refrigerator appliance 100 (e.g., within assembly recess 216) and the doors 128 are in the closed position.

Generally, storage container 212 extends along the vertical direction V between a bottom end 230 and a top end 232. Storage container 212 may further extend along the transverse direction T between a front end 234 proximal to a front surface of refrigerator door 128 (FIG. 1) and a rear end 236 proximal to a back portion of assembly recess 216 (e.g., when storage container 212 is received within assembly recess 216—FIG. 1). Between the bottom end 230 and the top end 232 sanitization chamber 214 is defined. For instance, sanitization chamber 214 may be defined by a container body 238 having a bottom wall 240 and a sidewall 242 extending upward therefrom. Optionally, one or more portions of container body 238 may include an insulating material (e.g., ceramic) to restrict heat transfer therethrough. When assembled, bottom wall 240 may extend along and define the lower limits of sanitization chamber 214 while sidewall 242 horizontally bounds (e.g., defines the horizontal limits of) sanitization chamber 214. In some embodiments, bottom wall 240 is provided as a perforated bottom wall 240 proximal to bottom end 230 (i.e., distal to top end 232) having multiple holes or apertures for permitting steam therethrough while preventing typical utensils, such as forks or knives, from falling out of sanitization chamber 214 through perforated bottom wall 240. Thus, perforated bottom wall 240 may be in fluid communication with sanitization chamber 214. Additionally or alternatively, perforated bottom wall 240 may be disposed below sanitization chamber 214.

Figure 7:
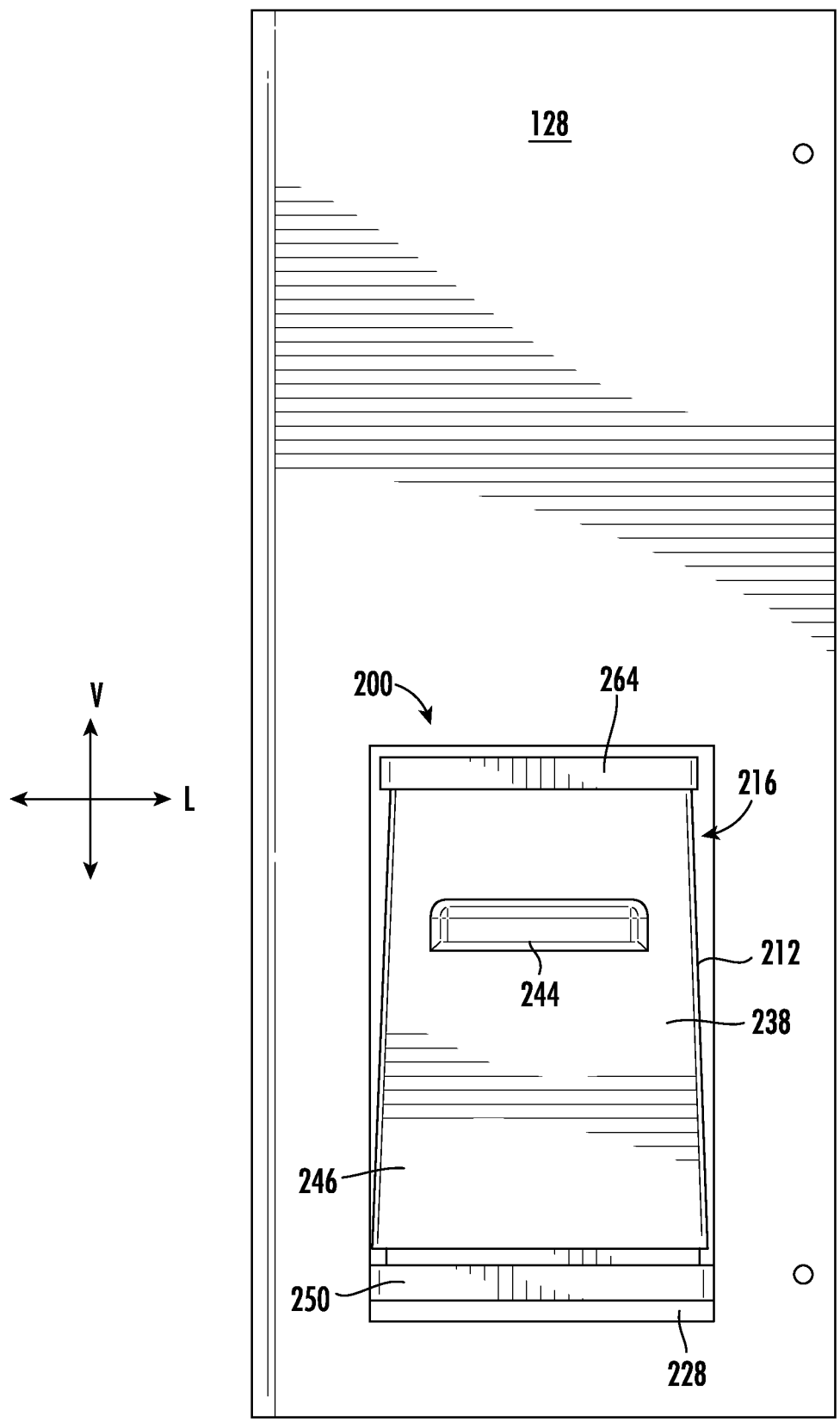
FIG. 7 provides a front elevation view of a storage container received within a door of a refrigerator appliance according to exemplary embodiments of the present disclosure.
Figure 8:
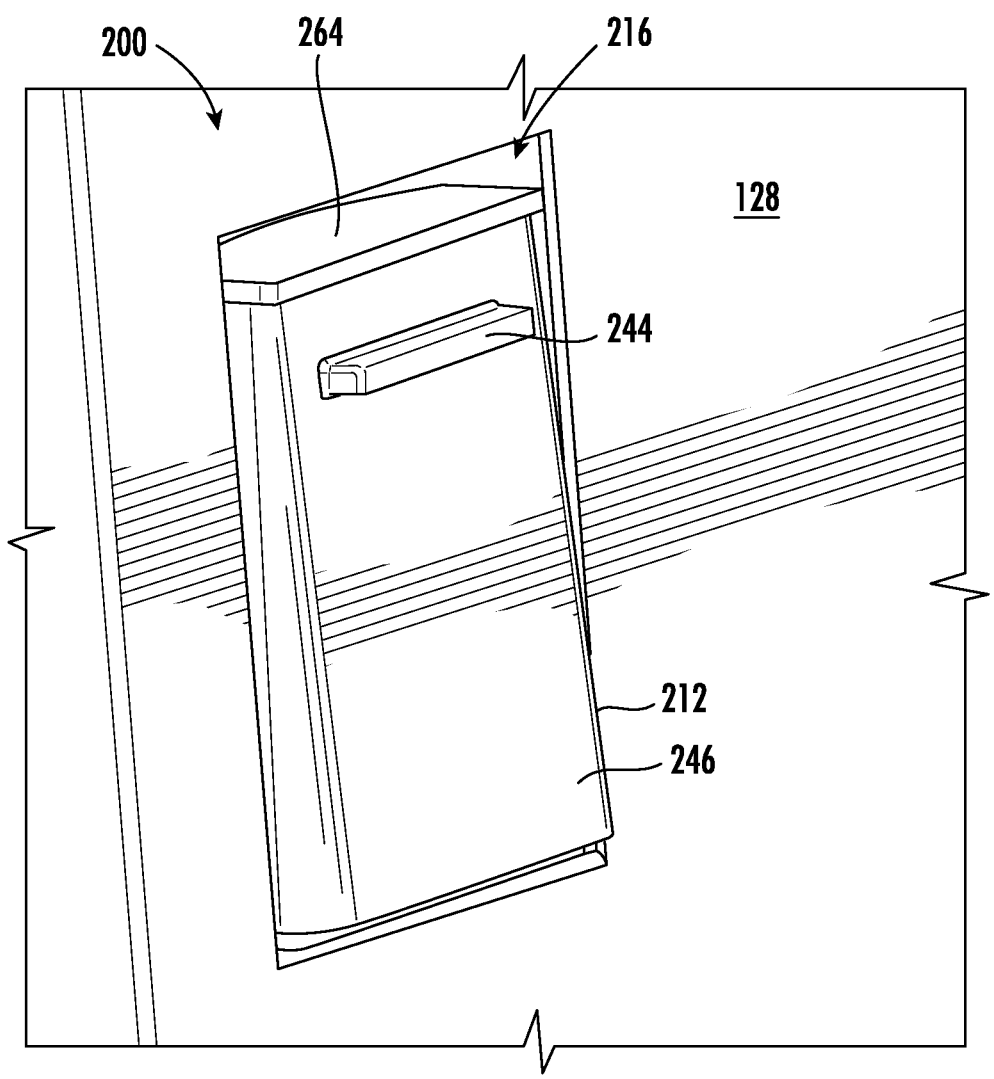
FIG. 8 provides a perspective view of the exemplary storage container of FIG. 7.

Turning briefly to FIGS. 7 and 8, optional embodiments of storage container 212 may include a handle 244. For instance, handle 244 may extend outward from sidewall 242. In some embodiments, handle 244 is disposed at front end 234. Thus, a user may grab handle 244 to selectively slide storage container 212 (e.g., along the transverse direction T) to or from assembly recess 216.

Returning especially to FIGS. 2 through 6, a container opening 246 may further be defined (e.g., by container body 238) to permit access to sanitization chamber 214 such that utensils can be freely inserted into or removed from sanitization chamber 214. For instance, container opening 246 may be defined by sidewall 242 at or proximal to top end 232 (e.g., along the vertical direction V).

Upstream from sanitization chamber 214, storage container 212 may define a fluid inlet 248. In certain embodiments, fluid inlet 248 is defined below or beneath sanitization chamber 214. For instance, a base plate 250 that supports container body 238 may define fluid inlet 248 at or proximal to the rear end 236. In some such embodiments, base plate 250 include a lower plate wall 252 and an upper rim 254 that extends upwards therefrom (e.g., to engage or hold container body 238). Together, lower plate wall 252 and upper rim 254 may define a liquid chamber 260 within which water may accumulate (e.g., prior to steam generation). Fluid inlet 248 may be defined upstream from liquid chamber 260 (e.g., through upper rim 254). Optionally, an electric heating element 256 of heater 210 may be mounted to base plate 250. Electric heating element 256 may be paired with heating plate 228 and received on the same (e.g., such that heating plate 228 and electric heating element 256 operate together to boil water and thereby generate steam, such as an electrically conductive or inductively coupled assembly).

During use, such as during a sanitization operation, base plate 250 (e.g., with or without an electrical heating element) may be disposed between heating plate 228 and sanitization chamber 214 along the vertical direction V. Prior to steam generation, refrigerator appliance 100 may direct a predefined volume of water to storage container 212. In particular, the water may be directed along one or more water conduits, including a supply line 258 within refrigerator appliance 100 that is in fluid communication with a water source (e.g., water tank, municipal water supply, well, etc.) upstream from supply line 258. An outlet of supply line 258 may be placed at or within assembly recess 216 (e.g., in alignment with fluid inlet 248 when storage container 212 is received within assembly recess 216). As would be understood, one or more water valves may be provided along or in fluid communication with supply line 258 to direct the flow of water therethrough. From supply line 258, the predefined volume of water may flow through fluid inlet 248 (e.g., to liquid chamber 260). Heater 210 may activated (e.g., for a predetermined heating period) such that the predefined volume of water boils, thereby generating steam that may rise or flow to sanitization chamber 214.

In order to permit steam to escape from sanitization chamber 214 (e.g., gradually during steam generation or after a predetermined period of time following the start of a sanitization operation), an exhaust outlet 262 is defined by storage container 212. For instance, exhaust outlet 262 may be defined at or proximal to top end 232 (e.g., separate or apart from container opening 246). In certain embodiments, a container lid 264 is provided to selectively cover container opening 246. Container lid 264 may thus be removably disposed over container opening 246 to seal the same. Optionally, exhaust outlet 262 may be defined through container lid 264 (e.g., at or proximal to rear end 236). In some such embodiments, container lid 264 comprises an upper wall 266 and a peripheral rim 268 that extends downward from upper wall 266. As shown, exhaust outlet 262 may be defined through peripheral rim 268 at or proximal to rear end 236.

Returning briefly to FIG. 1, an exhaust hose 270 may be mounted within refrigerator appliance 100 downstream from assembly recess 216. In particular, exhaust hose 270 may be mounted within the same door 128 as assembly recess 216 with an inlet that is disposed at or within assembly recess 216 (e.g., above the inlet of supply line 258). When storage container 212 is received within assembly recess 216, the inlet of exhaust hose 270 may be aligned with exhaust outlet 262. Steam supplied to sanitization chamber 214 may thus be permitted to exit storage container 212 through exhaust outlet 262 and to exhaust hose 270 (e.g., without passing directly through container opening 246). Exhaust hose 270 may extend to or terminate at a suitable outlet either within refrigerator appliance 100 (e.g., at evaporation pan 172) or outside of the refrigerator appliance 100 (e.g., a municipal sewage system).

Generally, exhaust hose 270 may include or be formed as any suitable conduit for directing steam through refrigerator door 128. In certain embodiments, a thermal damper 272 is mounted along exhaust hose 270. For instance, thermal damper 272 may be mounted within door 128 (e.g., the same door 128 as assembly recess 216) to draw heat from steam within exhaust hose 270. Thermal damper 272 may include a conductive, water-tolerant material (e.g., stainless steel, aluminum, etc.) that extends about or within the fluid passage defined by exhaust hose 270. Optionally, thermal damper 272 may include a high-surface-area structure (e.g., honeycomb) for directly contacting and condensing (e.g., passively) steam within exhaust hose 270. Additionally or alternatively, thermal damper 272 may include an insulating material about exhaust hose 270 for preventing the conduction of heat to one or more chilled chamber 122, 124.

Advantageously, a sanitizer assembly 200 in accordance with the present disclosure may permit a user to effectively sanitize utensils at a corresponding refrigerator appliance 100, such as immediately prior to use of such utensils, reducing or eliminating the potential for contamination prior to use. Such sanitization may be especially convenient and be performed without negatively impacting the temperature within the chilled chambers 122, 124.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A sanitizer assembly in downstream fluid communication with a refrigerator appliance, the sanitizer assembly comprising:
   a heating plate mounted on a door of the refrigerator appliance;
   a storage container disposed on the heating plate and extending between a bottom end and a top end, the storage container defining a sanitization chamber above the heating plate and a container opening at the top end to permit access to the sanitization chamber, wherein the storage container defines an exhaust outlet proximal to the top end to permit steam to exit the sanitization chamber, wherein the exhaust outlet is distinct from the container opening;
   an exhaust hose extending through the door in selective downstream fluid communication with the exhaust outlet; and
   a thermal damper mounted within the door along the exhaust hose, the thermal damper comprising a conductive material configured for condensing the steam into water droplets within the exhaust hose.

2. The sanitizer assembly of claim 1, wherein the storage container comprises a perforated bottom wall below the sanitization chamber to permit steam thereto.

3. The sanitizer assembly of claim 2, wherein the heating plate is disposed directly beneath the storage container.

4. The sanitizer assembly of claim 1, wherein the storage container further comprises a container lid removably disposed over the container opening, and wherein the exhaust outlet is defined through the container lid.

5. The sanitizer assembly of claim 4, wherein the container lid comprises an upper wall and a peripheral rim extending downward from the upper wall, and wherein the exhaust outlet is defined through the peripheral rim below the upper wall.

6. The sanitizer assembly of claim 1, wherein the heating plate is disposed beneath a fluid dispenser mounted to the door.

7. The sanitizer assembly of claim 1, further comprising an electric heating element removably received on the heating plate between the storage container and the heating plate.

8. A refrigerator appliance comprising:
   a cabinet defining a chilled chamber;
   an evaporation pan provided within the cabinet;

a door rotatably mounted on the cabinet to selectively restrict access to the chilled chamber, the door defining a container recess;

a heating plate mounted on the door at the container recess;

a storage container disposed within the container recess and extending between a bottom end and a top end, the storage container defining a sanitization chamber and a container opening between the top end and the bottom end, wherein the storage container defines an exhaust outlet to permit steam to exit the sanitization chamber; and an exhaust hose extending through the door in selective downstream fluid communication with the exhaust outlet, the exhaust hose terminating at the evaporation pan.

9. The refrigerator appliance of claim 8, wherein the storage container comprises a perforated bottom wall in fluid communication with the sanitization chamber to permit steam thereto.

10. The refrigerator appliance of claim 8, wherein the heating plate is disposed directly beneath the storage container.

11. The refrigerator appliance of claim 8, wherein the exhaust outlet is distinct from the container opening.

12. The refrigerator appliance of claim 11, wherein the storage container further comprises a container lid removably disposed over the container opening, and wherein the exhaust outlet is defined through the container lid.

13. The refrigerator appliance of claim 12, wherein the container lid comprises an upper wall and a peripheral rim extending downward from the upper wall, and wherein the exhaust outlet is defined through the peripheral rim below the upper wall.

14. The refrigerator appliance of claim 8, further comprising:

a thermal damper mounted within the door along the exhaust hose.

15. The refrigerator appliance of claim 8, wherein the heating plate is disposed beneath a fluid dispenser mounted to the door.

16. The refrigerator appliance of claim 8, further comprising an electric heating element removably received on the heating plate between the storage container and the heating plate.

* * * * *